United States Patent
Azzopardi et al.

(10) Patent No.: US 10,897,931 B2
(45) Date of Patent: Jan. 26, 2021

(54) VISUALIZATION SYSTEM AND METHOD FOR ELECTRONIC VAPOR PROVISION SYSTEMS

(71) Applicant: British American Tobacco (Investments) Limited, London (GB)

(72) Inventors: Anna Azzopardi, London (GB); Alfred Vincent Spencer, London (GB)

(73) Assignee: BRITISH AMERICAN TOBACCO (INVESTMENTS) LIMITED, London (GB)

(*) Notice: Subject to any disclaimer, the term of this patent is extended or adjusted under 35 U.S.C. 154(b) by 372 days.

(21) Appl. No.: 16/069,655

(22) PCT Filed: Dec. 9, 2016

(86) PCT No.: PCT/GB2016/053874
§ 371 (c)(1),
(2) Date: Jul. 12, 2018

(87) PCT Pub. No.: WO2017/121979
PCT Pub. Date: Jul. 20, 2017

(65) Prior Publication Data
US 2019/0000147 A1    Jan. 3, 2019

(30) Foreign Application Priority Data

Jan. 12, 2016    (GB) .................................. 1600539.9

(51) Int. Cl.
*A24F 15/06*    (2006.01)
*A24F 47/00*    (2020.01)
(Continued)

(52) U.S. Cl.
CPC ........... *A24F 47/008* (2013.01); *A61M 15/06* (2013.01); *A61M 11/042* (2014.02);
(Continued)

(58) Field of Classification Search
CPC ............... A24F 47/008; A61M 11/042; A61M 2016/0027; A61M 2205/3584;
(Continued)

(56) References Cited

U.S. PATENT DOCUMENTS 4,366,821 A  *  1/1983  Wittmaier ............... A61B 5/113
                                                  340/573.1
6,809,743 B2    10/2004  Ebersole
(Continued)

FOREIGN PATENT DOCUMENTS

EP    0667168 A1    8/1995
EP    1847287 A1    10/2007
(Continued)

OTHER PUBLICATIONS

Dialog DA14580, *Lower Power Bluetooth Smart SoC*. Available at: http://www.dialog-semiconductor.com/products/bluetooth-smart/smartbond-da14580, © 2014, 158 pages.
(Continued)

*Primary Examiner* — Ojiako K Nwugo
(74) *Attorney, Agent, or Firm* — Patterson Thuente Pedersen, P.A.

(57) ABSTRACT

A method of visualization between an electronic vapor provision system and a visualization device includes obtaining from the electronic vapor provision system notification that an inhalation on the electronic vapor provision system by a user has occurred, estimating a time of exhalation by the user responsive to the time of notification, and initiating a display of a computer graphic by the visualization device responsive to the estimated time of exhalation.

17 Claims, 8 Drawing Sheets

(51) Int. Cl.
*A61M 15/06* (2006.01)
*A61M 16/00* (2006.01)
*A61M 11/04* (2006.01)
*G06F 3/147* (2006.01)
*G06F 9/54* (2006.01)

(52) U.S. Cl.
CPC .............. *A61M 2016/0027* (2013.01); *A61M 2205/3569* (2013.01); *A61M 2205/3584* (2013.01); *A61M 2205/3592* (2013.01); *A61M 2205/505* (2013.01); *A61M 2205/507* (2013.01); *A61M 2205/581* (2013.01); *A61M 2205/583* (2013.01); *A61M 2205/8206* (2013.01); *G06F 3/147* (2013.01); *G06F 9/542* (2013.01)

(58) Field of Classification Search
CPC .... A61M 2205/3592; A61M 2205/505; A61M 2205/507; A61M 2205/581; A61M 2205/583; A61M 2205/8206; G06F 3/147; G06F 9/542
USPC ........................................................ 340/815
See application file for complete search history.

(56) References Cited

U.S. PATENT DOCUMENTS

| | | | |
|---|---|---|---|
| 2007/0006889 A1 | 1/2007 | Kobal | |
| 2012/0199146 A1* | 8/2012 | Marangos | A24F 47/008 131/328 |
| 2012/0247235 A1* | 10/2012 | Adamo | G09B 23/28 73/865.4 |
| 2013/0276799 A1 | 10/2013 | Davidson | |
| 2014/0107815 A1 | 4/2014 | LaMothe | |
| 2014/0116455 A1 | 5/2014 | Hong | |
| 2015/0075546 A1 | 3/2015 | Kueny | |
| 2015/0173419 A1* | 6/2015 | Tu | A24F 47/008 131/329 |
| 2015/0245654 A1 | 9/2015 | Memari | |
| 2015/0327596 A1 | 11/2015 | Alarcon | |
| 2018/0270311 A1 | 9/2018 | Baker | |
| 2018/0270643 A1 | 9/2018 | Baker | |
| 2018/0280640 A1 | 10/2018 | Baker | |
| 2018/0286208 A1 | 10/2018 | Baker | |
| 2018/0303163 A1 | 10/2018 | Baker | |

FOREIGN PATENT DOCUMENTS

| | | |
|---|---|---|
| JP | 2003250509 A | 9/2003 |
| JP | 2015532112 | 11/2015 |
| WO | WO2011003017 A1 | 1/2011 |
| WO | WO2011083377 A1 | 7/2011 |
| WO | WO2014125483 A1 | 8/2014 |

OTHER PUBLICATIONS

Bluetooth Smart, Bluebooth Low Energy, *Bluetooth Smart Technology: Powering the Internet of Things*, Available at: http://www.bluetooth.com/Pages/Bluetooth-Smart.aspx, dated Nov. 10, 2014, 2 pages.
ISO/IEC 13157 Information Technology—Telecommunications and Information Exchange Between Systems—NFC Security Part 1 NFC-SEC NFCIP-1 Security Services and Protocol, dated Aug. 15, 2014, 2 pages.
IEEE802.11ah IEEE Draft Standard for Information Technology—Telecommunications and Information Exchange between Systems—Local and Metropolitan Area networks—Specific Requirements—Part 11: Wireless LAN Medium Access Control (MAC) and Physical Layer, dated Feb. 2016, 1 page.
IEEE 802.11v Standard for Information Technology—Telecommunications and Information Exchange between systems—Local and Metropolitan networks: Amendment 8: Wireless LAN Medium Access Control (MAC) and Physical Layer (PHY) specification: Wireless Network Management , dated May 13, 2011, 1 page.
Great Britain Search Report, Application No. GB1600539.9, dated Mar. 31, 2016, 3 pages.
International Search Report and Written Opinion, Application No. PCT/GB2016/053874, dated Apr. 13, 2017, 15 pages.
Partial Search Report, Application No. PCT/GB2016/053874, dated Feb. 16, 2017, 5 pages.
International Preliminary Report on Patentability, Application No. PCT/GB2016/053874, dated Jul. 26, 2018, 12 pages.
Japanese Office Action, Application No. 2018-536117, dated Jul. 1, 2019, 8 pages.

* cited by examiner

US 10,897,931 B2

VISUALIZATION SYSTEM AND METHOD FOR ELECTRONIC VAPOR PROVISION SYSTEMS

PRIORITY CLAIM

The present application is a National Phase entry of PCT Application No. PCT/GB2016/053874, filed Dec. 9, 2016, which claims priority from GB Patent Application No. 1600539.9, filed Jan. 12, 2016, which is hereby fully incorporated herein by reference.

FIELD

The present disclosure relates to a visualization system and method for electronic vapor provision systems such as electronic nicotine delivery systems (e.g. e-cigarettes).

BACKGROUND

Electronic vapor provision systems, such as e-cigarettes and other aerosol delivery systems, generally contain a reservoir of liquid which is to be vaporized, often comprising nicotine (this is sometimes referred to as an "e-liquid"), or a solid substrate comprising materials that may be vaporized by heating (for example in the case of tobacco heating products that heat but do not burn tobacco). When a user inhales on the device, an electrical (e.g. resistive) heater is activated to vaporize a small amount of material (for example, liquid), in effect producing an aerosol which is therefore inhaled by the user. The liquid may comprise nicotine in a solvent, such as ethanol or water, together with glycerine or propylene glycol to aid aerosol formation, and may also include one or more additional flavors. The skilled person will be aware of many different liquid formulations that may be used in e-cigarettes and other such devices.

The practice of inhaling vaporized liquid or solid material in this manner is commonly known as "vaping." For convenience only, the following description primarily refers to liquid based electronic vapor provision systems.

An e-cigarette may have an interface to support external data communications. This interface may be used, for example, to load control parameters and/or updated software onto the e-cigarette from an external source. Alternatively or additionally, the interface may be utilized to download data from the e-cigarette to an external system. The downloaded data may, for example, represent usage parameters of the e-cigarette, fault conditions, etc. As the skilled person will be aware, many other forms of data can be exchanged between an e-cigarette and one or more external systems (which may be another e-cigarette).

In some cases, the interface for an e-cigarette to perform communication with an external system is based on a wired connection, such as a USB link using a micro, mini, or ordinary USB connection into the e-cigarette. The interface for an e-cigarette to perform communication with an external system may also be based on a wireless connection. Such a wireless connection has certain advantages over a wired connection. For example, a user does not need any additional cabling to form such a connection. In addition, the user has more flexibility in terms of movement, setting up a connection, and the range of pairing devices.

Note that many e-cigarettes already provide support for a USB interface in order to allow the e-cigarette to be recharged. Accordingly, the additional use of such a wired interface to also provide data communications is relatively straightforward. However, the situation for providing a wireless data connection is more complex.

Furthermore, there is scope for e-cigarettes to exploit such wired or wireless connections to improve the vaping experience for the user.

SUMMARY

In one aspect of the present disclosure, there is provided method of visualization between an electronic vapor provision system and a visualization device.

In another aspect of the present disclosure, there is provided method of visualization between an electronic vapor provision system and a visualization device.

In another aspect of the present disclosure, there is provided an electronic vapor provision system.

In another aspect of the present disclosure, there is provided a visualization device.

In another aspect of the present disclosure, there is provided a visualization device.

In another aspect of the present disclosure, there is provided a visualization system.

Further respective aspects and features of the disclosure are defined in the appended claims.

BRIEF DESCRIPTION OF THE DRAWINGS

Embodiments of the present disclosure will now be described by way of example with reference to the accompanying drawings, in which.

DETAILED DESCRIPTION

A visualization system and method for electronic vapor provision systems are disclosed. In the following description, a number of specific details are presented in order to provide a thorough understanding of the embodiments of the present disclosure. It will be apparent, however, to a person skilled in the art that these specific details need not be employed to practice the present disclosure. Conversely, specific details known to the person skilled in the art are omitted for the purposes of clarity where appropriate.

As described above, the present disclosure relates to an electronic vapor provision system, such as an e-cigarette. Throughout the following description the term "e-cigarette" is used; however, this term may be used interchangeably with electronic vapor provision system, aerosol delivery device, and other similar terminology.

Figure 1:
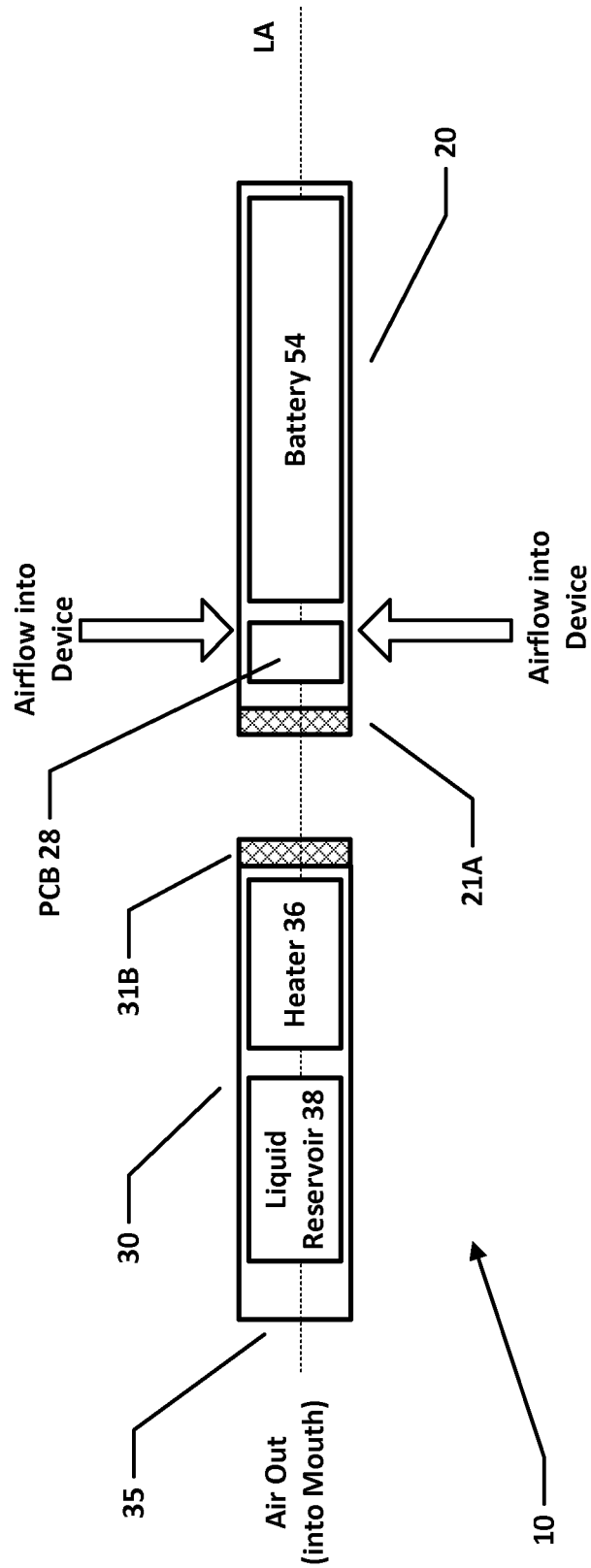
FIG. 1 is a schematic (exploded) diagram of an e-cigarette in accordance with some embodiments of the disclosure.

FIG. 1 is a schematic (exploded) diagram of an e-cigarette 10 in accordance with some embodiments of the disclosure (not to scale). The e-cigarette 10 comprises a body or control unit 20 and a cartomizer 30. The cartomizer 30 includes a reservoir 38 of liquid, typically including nicotine, a heater 36, and a mouthpiece 35. The e-cigarette 10 has a longitudinal or cylindrical axis which extends along the center-line of the e-cigarette 10 from the mouthpiece 35 at one end of the cartomizer 30 to the opposing end of the control unit 20 (usually referred to as the tip end). This longitudinal axis is indicated in FIG. 1 by the dashed line denoted LA.

The liquid reservoir 38 in the cartomizer 30 may hold the (e-)liquid directly in liquid form, or may utilize some absorbing structure, such as a foam matrix or cotton material, etc., as a retainer for the liquid. The liquid is then fed from the reservoir 38 to be delivered to a vaporizer comprising the heater 36. For example, liquid may flow via capillary action from the reservoir 38 to the heater 36 via a wick (not shown in FIG. 1).

In other devices, the liquid may be provided in the form of plant material or some other (ostensibly solid) plant derivative material. In this case the liquid can be considered as representing volatiles in the material which vaporize when the material is heated. Note that devices containing this type of material generally do not require a wick to transport the liquid to the heater, but rather provide a suitable arrangement of the heater in relation to the material to provide suitable heating.

The control unit 20 includes a re-chargeable cell or battery 54 to provide power to the e-cigarette 10 (referred to hereinafter as a battery) and a printed circuit board (PCB) 28 and/or other electronics for generally controlling the e-cigarette 10.

The control unit 20 and the cartomizer 30 are detachable from one another, as shown in FIG. 1, but are joined together when the device 10 is in use, for example, by a screw or bayonet fitting. The connectors on the cartomizer 30 and the control unit 20 are indicated schematically in FIG. 1 as 31B and 21A respectively. This connection between the control unit 20 and cartomizer 30 provides for mechanical and electrical connectivity between the two.

When the control unit 20 is detached from the cartomizer 30, the electrical connection 21A on the control unit 20 that is used to connect to the cartomizer 30 may also serve as a socket for connecting a charging device (not shown). The other end of this charging device can be plugged into a USB socket to re-charge the battery 54 in the control unit of the e-cigarette 10. In other implementations, the e-cigarette 10 may be provided (for example) with a cable for direct connection between the electrical connection 21A and a USB socket.

The control unit 20 is provided with one or more holes for air inlet adjacent to PCB 28. These holes connect to an air passage through the control unit 20 to an air passage provided through the connector 21A. This then links to an air path through the cartomizer 30 to the mouthpiece 35. Note that the heater 36 and the liquid reservoir 38 are configured to provide an air channel between the connector 31B and the mouthpiece 35. This air channel may flow through the center of the cartomizer 30, with the liquid reservoir 38 confined to an annular region around this central path. Alternatively (or additionally) the airflow channel may lie between the liquid reservoir 38 and an outer housing of the cartomizer 30.

When a user inhales through the mouthpiece 35, air is drawn into the control unit 20 through the one or more air inlet holes. This airflow (or the associated change in pressure) is detected by a sensor, e.g. a pressure sensor, which in turn activates the heater 36 to vaporize the nicotine liquid fed from the reservoir 38. The airflow passes from the control unit 20 into the vaporizer, where the airflow combines with the nicotine vapor. This combination of airflow and nicotine vapor (in effect, an aerosol) then passes through the cartomizer 30 and out of the mouthpiece 35 to be inhaled by a user. The cartomizer 30 may be detached from the control unit 20 and disposed of when the supply of nicotine liquid is exhausted (and then replaced with another cartomizer).

It will be appreciated that the e-cigarette 10 shown in FIG. 1 is presented by way of example only, and many other implementations may be adopted. For example, in some implementations, the cartomizer 30 is split into a cartridge containing the liquid reservoir 38 and a separate vaporizer portion containing the heater 36. In this configuration, the cartridge may be disposed of after the liquid in reservoir 38 has been exhausted, but the separate vaporizer portion containing the heater 36 is retained. Alternatively, an e-cigarette may be provided with a cartomizer 30 as shown in FIG. 1, or else constructed as a one-piece (unitary) device, but the liquid reservoir 38 is in the form of a (user-)replaceable cartridge. Further possible variations are that the heater 36 may be located at the opposite end of the cartomizer 30 from that shown in FIG. 1, i.e. between the liquid reservoir 38 and the mouthpiece 35, or else the heater 36 is located along a central axis LA of the cartomizer 30, and the liquid reservoir 38 is in the form of an annular structure which is radially outside the heater 35.

The skilled person will also be aware of a number of possible variations for the control unit 20. For example, airflow may enter the control unit 20 at the tip end, i.e. the opposite end to connector 21A, in addition to or instead of the airflow adjacent to PCB 28. In this case the airflow would typically be drawn towards the cartomizer 30 along a passage between the battery 54 and the outer wall of the control unit 20. Similarly, the control unit 20 may comprise a PCB located on or near the tip end, e.g. between the battery and the tip end. Such a PCB may be provided in addition to or instead of PCB 28.

Furthermore, an e-cigarette 10 may support charging at the tip end, or via a socket elsewhere on the device, in addition to or in place of charging at the connection point between the cartomizer 30 and the control unit 20. (It will be appreciated that some e-cigarettes are provided as essentially integrated units, in which case a user is unable to disconnect the cartomizer from the control unit.) Other e-cigarettes may also support wireless (induction) charging, in addition to (or instead of) wired charging.

The above discussion of potential variations to the e-cigarette 10 shown in FIG. 1 is by way of example. The skilled person will aware of further potential variations (and combination of variations) for the e-cigarette 10.

Figure 2:
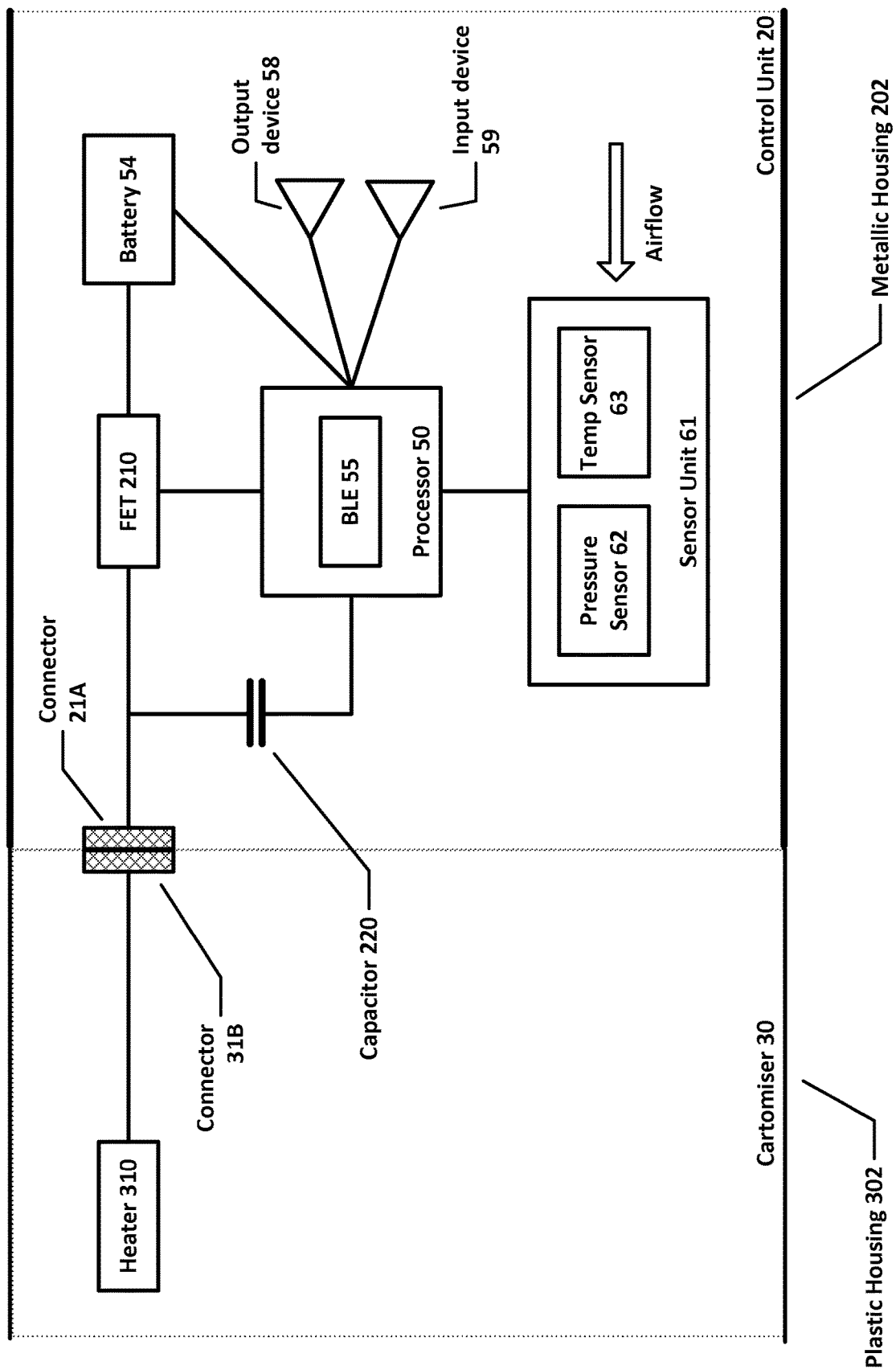
FIG. 2 is a schematic diagram of the main electrical/electronic components of the e-cigarette of FIG. 1 in accordance with some embodiments of the disclosure.

FIG. 2 is a schematic diagram of the main functional components of the e-cigarette 10 of FIG. 1 in accordance with some embodiments of the disclosure. N.B. FIG. 2 is primarily concerned with electrical connectivity and functionality—it is not intended to indicate the physical sizing of the different components, nor details of their physical placement within the control unit 20 or cartomizer 30. In addition, it will be appreciated that at least some of the components shown in FIG. 2 located within the control unit 20 may be mounted on the circuit board 28. Alternatively, one or more of such components may instead be accommodated in the control unit 20 to operate in conjunction with the circuit board 28, but not physically mounted on the circuit board itself. For example, these components may be located on one or more additional circuit boards, or they may be separately located (such as battery 54).

As shown in FIG. 2, the cartomizer 30 contains heater 310 which receives power through connector 31B. The control unit 20 includes an electrical socket or connector 21A for connecting to the corresponding connector 31B of the cartomizer 30 (or potentially to a USB charging device). This then provides electrical connectivity between the control unit 20 and the cartomizer 30.

The control unit 20 further includes a sensor unit 61, which is located in or adjacent to the air path through the control unit 20 from the air inlet(s) to the air outlet (to the cartomizer 30 through the connector 21A). The sensor unit 61 contains a pressure sensor 62 and temperature sensor 63 (also in or adjacent to this air path). The control unit 20 further includes a capacitor 220, a processor 50, a field effect transistor (FET) switch 210, a battery 54, and input and output devices 59, 58.

The operations of the processor 50 and other electronic components, such as the pressure sensor 62, are generally controlled at least in part by software programs running on the processor 50 (or other components). Such software programs may be stored in non-volatile memory, such as ROM, which can be integrated into the processor 50 itself, or provided as a separate component. The processor 50 may access the ROM to load and execute individual software programs as and when required. The processor 50 also contains appropriate communications facilities, e.g. pins or pads (plus corresponding control software), for communicating as appropriate with other devices in the control unit 20, such as the pressure sensor 62.

The output device(s) 58 may provide visible, audio and/or haptic output. For example, the output device(s) 58 may include a speaker, a vibrator, and/or one or more lights. The lights are typically provided in the form of one or more light emitting diodes (LEDs), which may be the same or different colors (or multi-colored). In the case of multi-colored LEDs, different are obtained by switching red, green or blue LEDs on, optionally at different relative brightnesses to give corresponding relative variations in color. Where red, green and blue LEDs are provided together, a full range of colors is possible, whilst if only two out of the three red, green and blue LEDs are provided, only a respective sub-range of colors can be obtained.

The output from the output device 58 may be used to signal to the user various conditions or states within the e-cigarette 10, such as a low battery warning. Different output signals may be used for signaling different states or conditions. For example, if the output device 58 is an audio speaker, different states or conditions may be represented by tones or beeps of different pitch and/or duration, and/or by providing multiple such beeps or tones. Alternatively, if the output device 58 includes one or more lights, different states or conditions may be represented by using different colors, pulses of light or continuous illumination, different pulse durations, and so on. For example, one indicator light might be utilized to show a low battery warning, while another indicator light might be used to indicate that the liquid reservoir 58 is nearly depleted. It will be appreciated that a given e-cigarette may include output devices to support multiple different output modes (audio, visual, etc.).

The input device(s) 59 may be provided in various forms. For example, an input device (or devices) 59 may be implemented as buttons on the outside of the e-cigarette 10—e.g. as mechanical, electrical or capacitor (touch) sensors. Some devices 59 may support blowing into the e-cigarette 10 as an input mechanism (such blowing may be detected by pressure sensor 62, which would then be also acting as a form of input device 59), and/or connecting/disconnecting the cartomizer 30 and control unit 20 as another form of input mechanism 59. Again, it will be appreciated that a given e-cigarette may include input devices 59 to support multiple different input modes.

As noted above, the e-cigarette 10 provides an air path from the air inlet through the e-cigarette 10, past the pressure sensor 62 and the heater 310 in the cartomizer 30 to the mouthpiece 35. Thus when a user inhales on the mouthpiece 35 of the e-cigarette 10, the processor 50 detects such inhalation based on information from the pressure sensor 62. In response to such a detection, the CPU supplies power from the battery 54 to the heater, which thereby heats and vaporizes the nicotine from the liquid reservoir 38 for inhalation by the user. Meanwhile for example, for a device which is button activated, a different air path may be used (for example not entering the battery section).

In the particular implementation shown in FIG. 2, a FET 210 is connected between the battery 54 and the connector 21A. This FET 210 acts as a switch. The processor 50 is connected to the gate of the FET 210 to operate the switch, thereby allowing the processor 50 to switch on and off the flow of power from the battery 54 to heater 310 according to the status of the detected airflow. It will be appreciated that the heater current can be relatively large, for example, in the range 1-5 amps, and hence the FET 210 should be implemented to support such current control (likewise for any other form of switch that might be used in place of FET 210).

In order to provide more fine-grained control of the amount of power flowing from the battery 54 to the heater 310, a pulse-width modulation (PWM) scheme may be adopted. A PWM scheme may be based on a repetition period of say 1 ms. Within each such period, the switch 210 is turned on for a proportion of the period, and turned off for the remaining proportion of the period. This is parameterized by a duty cycle, whereby a duty cycle of 0 indicates that the switch is off for all of each period (i.e. in effect, permanently off), a duty cycle of 0.33 indicates that the switch is on for a third of each period, a duty cycle of 0.66 indicates that the switch is on for two-thirds of each period, and a duty cycle of 1 indicates that the FET 210 is on for all of each period (i.e. in effect, permanently on). It will be appreciated that these are only given as example settings for the duty cycle, and intermediate values can be used as appropriate.

The use of PWM provides an effective power to the heater 310 which is given by the nominal available power (based on the battery output voltage and the heater resistance) multiplied by the duty cycle. The processor 50 may, for example, utilize a duty cycle of 1 (i.e. full power) at the start of an inhalation to initially raise the heater 310 to its desired operating temperature as quickly as possible. Once this desired operating temperature has been achieved, the processor 50 may then reduce the duty cycle to some suitable value in order to maintain the heater 310 at the desired operating temperature.

As shown in FIG. 2, the processor 50 includes a communications interface 55 for wireless communications, in particular, support for Bluetooth® Low Energy (BLE) communications.

Optionally the heater 310 may be utilized as an antenna for use by the communications interface 55 for transmitting and receiving the wireless communications. One motivation for this is that the control unit 20 may have a metal housing 202, whereas the cartomizer portion 30 may have a plastic housing 302 (reflecting the fact that the cartomizer 30 is disposable, whereas the control unit 20 is retained and therefore needs to be more durable). The metal housing 202 acts as a screen or barrier which makes it difficult to locate an antenna within the control unit 20 itself. However, utilizing the heater 310 as the antenna for the wireless communications avoids this metal screening because of the plastic housing of the cartomizer 30, but without adding additional components or complexity (or cost) to the cartomizer 30. Alternatively a separate antenna may be provided (not shown), or a portion of the metal housing 202 may be used.

If the heater 310 is used as an antenna then as shown in FIG. 2, the processor 50, more particularly the communications interface 55, may be coupled to the power line from the battery 54 to the heater 310 (via connector 31B) by a capacitor 220. This capacitive coupling occurs downstream of the switch 210, since the wireless communications may operate when the heater 310 is not powered for heating (as discussed in more detail below). It will be appreciated that capacitor 220 prevents the power supply from the battery 54 to the heater 310 being diverted back to the processor 50.

Note that the capacitive coupling may be implemented using a more complex LC (inductor-capacitor) network, which can also provide impedance matching with the output of the communications interface 55. (As known to the person skilled in the art, this impedance matching supports proper transfer of signals between the communications interface 55 and the heater 310 acting as the antenna, rather than having such signals reflected back along the connection.)

In some implementations, the processor 50 and communications interface 55 are implemented using a Dialog DA14580 chip from Dialog Semiconductor PLC, based in Reading, United Kingdom. Further information (and a data sheet) for this chip is available at www.dialog-semiconductor.com.

Figure 3:
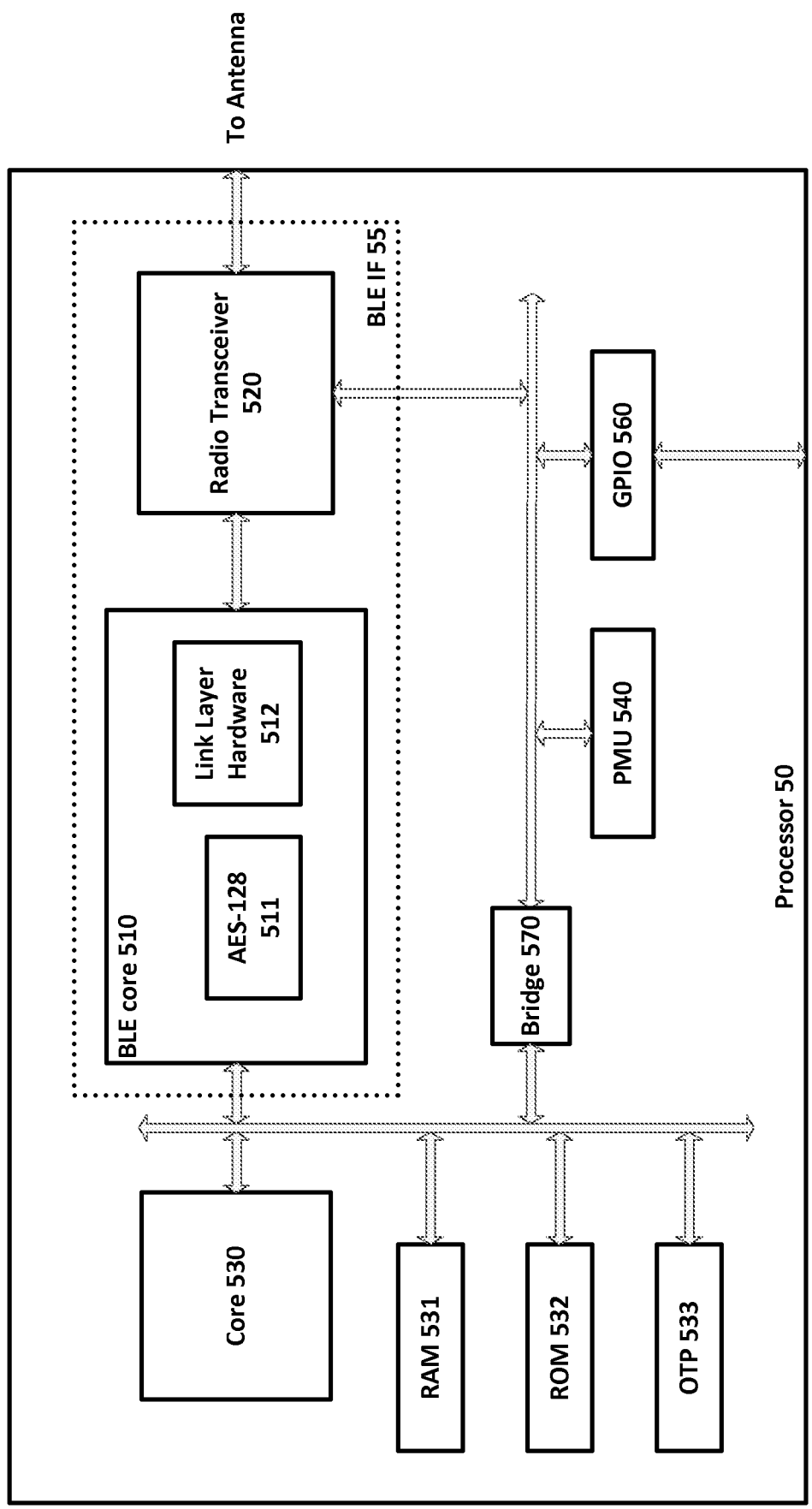
FIG. 3 is a simplified schematic diagram of the processor of the e-cigarette of FIG. 1 in accordance with some embodiments of the disclosure.

FIG. 3 presents a high-level and simplified overview of this chip 50, including the communications interface 55 for supporting Bluetooth® Low Energy. This interface 55 includes in particular a radio transceiver 520 for performing signal modulation and demodulation, etc., link layer hardware 512, and an advanced encryption facility (128 bits) 511. The output from the radio transceiver 520 is connected to the antenna (for example, to the heater 310 acting as the antenna via capacitive coupling 220 and connectors 21A and 31B).

The remainder of processor 50 includes a general processing core 530, RAM 531, ROM 532, a one-time programming (OTP) unit 533, a general purpose I/O system 560 (for communicating with other components on the PCB 28), a power management unit 540 and a bridge 570 for connecting two buses. Software instructions stored in the ROM 532 and/or OTP unit 533 may be loaded into RAM 531 (and/or into memory provided as part of core 530) for execution by one or more processing units within core 530. These software instructions cause the processor 50 to implement various functionality described herein, such as interfacing with the sensor unit 61 and controlling the heater accordingly. Note that although the device shown in FIG. 3 acts as both a communications interface 55 and also as a general controller for the electronic vapor provision system 10, in other embodiments these two functions may be split between two or more different devices (chips)—e.g. one chip may serve as the communications interface 55, and another chip as the general controller for the electronic vapor provision system 10.

In some implementations, the processor 50 may be configured to prevent wireless communications when the heater 310 is being used for vaporizing liquid from reservoir 38. For example, wireless communications may be suspended, terminated or prevented from starting when switch 210 is switched on. Conversely, if wireless communications are ongoing, then activation of the heater 310 may be prevented—e.g. by discarding a detection of airflow from the sensor unit 61, and/or by not operating switch 210 to turn on power to the heater 310 while the wireless communications are progressing.

One reason for preventing the simultaneous operation of heater 310 for both heating and wireless communications is to avoid any potential interference from the PWM control of the heater 310. This PWM control has its own frequency (based on the repetition frequency of the pulses), albeit much lower than the frequency of the wireless communications, and the two could potentially interfere with one another. In some situations, such interference may not, in practice, cause any problems, and simultaneous operation of heater 310 for both heating and wireless communications may be allowed (if so desired). This may be facilitated, for example, by techniques such as the appropriate selection of signal strengths and/or PWM frequency, the provision of suitable filtering, etc.

Figure 4:
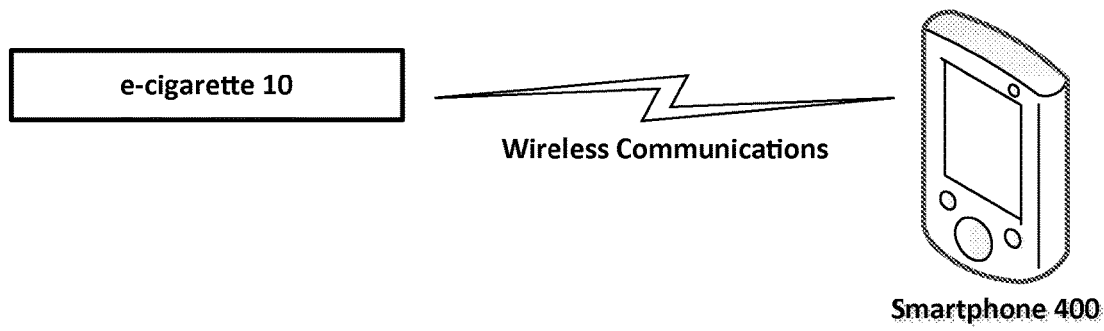
FIG. 4 is a schematic diagram of wireless communications between the e-cigarette of FIG. 1 and a mobile communication device.

FIG. 4 is a schematic diagram showing Bluetooth® Low Energy communications between an e-cigarette 10 and an application (app) running on a smartphone 400 or other suitable mobile communication device (tablet, laptop, smartwatch, etc). Such communications can be used for a wide range of purposes, for example, to upgrade firmware on the e-cigarette 10, to retrieve usage and/or diagnostic data from the e-cigarette 10, to reset or unlock the e-cigarette 10, to control settings on the e-cigarette 10, etc.

In general terms, when the e-cigarette 10 is switched on, such as by using input device 59, or possibly by joining the cartomizer 30 to the control unit 20, it starts to advertise for Bluetooth® Low Energy communication. If this outgoing communication is received by smartphone 400, then the smartphone 400 requests a connection to the e-cigarette 10. The e-cigarette 10 may notify this request to a user via output device 58, and wait for the user to accept or reject the request via input device 59. Assuming the request is accepted, the e-cigarette 10 is able to communicate further with the smartphone 400. Note that the e-cigarette 10 may remember the identity of smartphone 400 and be able to accept future connection requests automatically from that smartphone 400. Once the connection has been established, the smartphone 400 and the e-cigarette 10 operate in a client-server mode, with the smartphone 400 operating as a client that initiates and sends requests to the e-cigarette 10 which therefore operates as a server (and responds to the requests as appropriate).

A Bluetooth® Low Energy link (also known as Bluetooth Smart®) implements the IEEE 802.15.1 standard, and operates at a frequency of 2.4-2.5 GHz, corresponding to a wavelength of about 12 cm, with data rates of up to 1 Mbit/s. The set-up time for a connection is less than 6 ms, and the average power consumption can be very low—of the order 1 mW or less. A Bluetooth Low Energy link may extend up to some 50 m. However, for the situation shown in FIG. 4, the e-cigarette 10 and the smartphone 400 will typically belong to the same person, and will therefore be in much closer proximity to one another—e.g. 1 m. Further information about Bluetooth® Low Energy can be found at www.bluetooth.com.

It will be appreciated that e-cigarette 10 may support other communications protocols for communication with smartphone 400 (or any other appropriate device). Such other communications protocols may be instead of, or in addition to, Bluetooth® Low Energy. Examples of such other communications protocols include Bluetooth® (not the low energy variant), see for example, www.bluetooth.com, near field communications (NFC), as per ISO 13157, and WiFi®. NFC communications operate at much lower wavelengths than Bluetooth® (13.56 MHz) and generally have a much shorter range—say <0.2 m. However, this short range is still compatible with most usage scenarios such as shown in FIG. 4. Meanwhile, low-power WiFi® communications, such as IEEE802.11ah, IEEE802.11v, or similar, may be employed between the e-cigarette 10 and a remote device. In each case, a suitable communications chipset may be included on PCB 28, either as part of the processor 50 or as a separate component. The skilled person will be aware of other wireless communication protocols that may be employed in e-cigarette 10.

Figure 5:
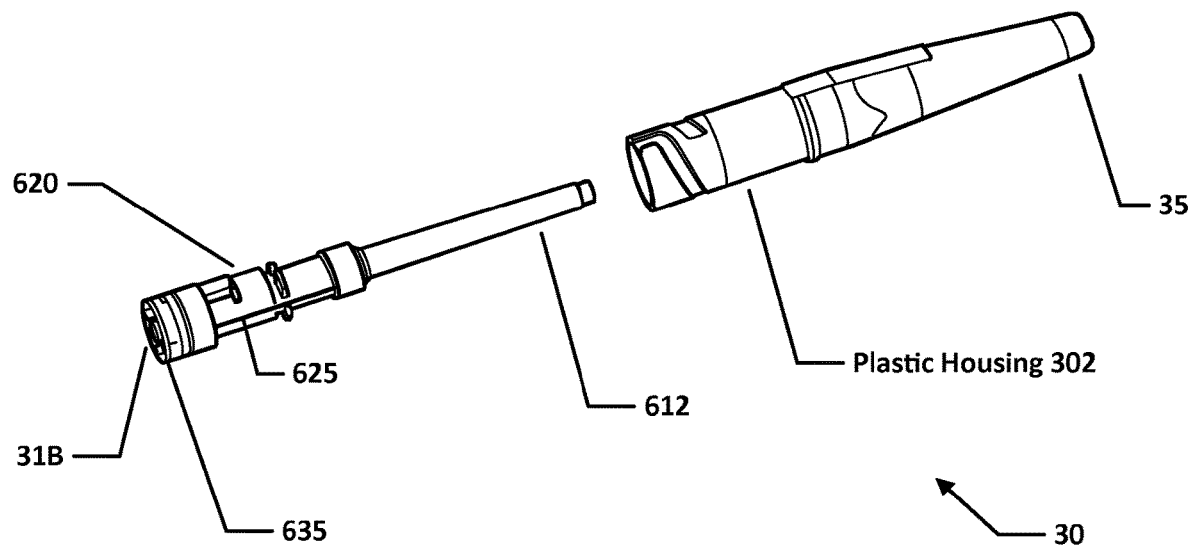
FIG. 5 is a schematic (exploded) diagram of the cartomizer of an e-cigarette in accordance with some embodiments of the disclosure.

FIG. 5 is a schematic, exploded view of an example cartomizer 30 in accordance with some embodiments. The cartomizer 30 has an outer plastic housing 302, a mouthpiece 35 (which may be formed as part of the housing), a vaporizer 620, a hollow inner tube 612, and a connector 31B for attaching to a control unit 20. An airflow path through the cartomizer 30 starts with an air inlet through connector 31B, then through the interior of vaporizer 625 and hollow tube 612, and finally out through the mouthpiece 35. The cartomizer 30 retains liquid in an annular region between (i) the plastic housing 302, and (ii) the vaporizer 620 and the inner tube 612. The connector 31B is provided with a seal 635 to help maintain liquid in this region and to prevent leakage.

Figure 6:
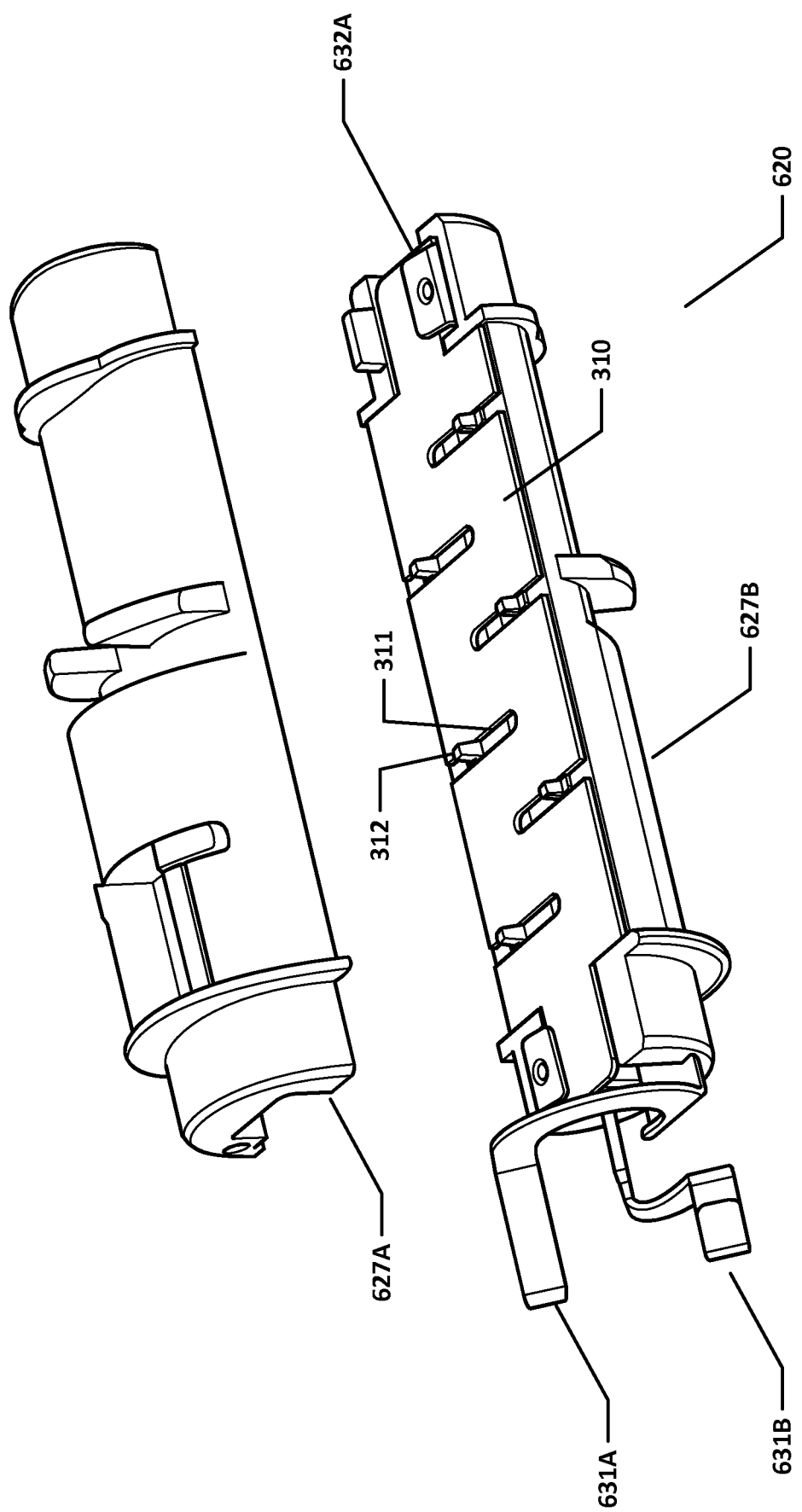
FIG. 6 is a schematic (exploded) diagram of the vaporizer from the cartomizer of FIG. 5 in accordance with some embodiments of the disclosure.

FIG. 6 is a schematic, exploded view of the vaporizer 620 from the example cartomizer 30 shown in FIG. 5. The vaporizer 620 has a substantially cylindrical housing (cradle) formed from two components, 627A, 627B, each having a substantially semi-circular cross-section. When assembled, the edges of the components 627A, 627B do not completely abut one another (at least, not along their entire length), but rather a slight gap 625 remains (as indicated in FIG. 5). This gap allows liquid from the outer reservoir around the vaporizer and tube 612 to enter into the interior of the vaporizer 620.

One of the components 627B of the vaporizer supports a heater 310. There are two connectors 631A, 631B shown for supplying power (and a wireless communication signal) to the heater 310. More particular, these connectors 631A, 631B link the heater 310 to connector 31B, and from there to the control unit 20. (Note that connector 631A is joined to pad 632A at the far end of vaporizer 620 from connector 31B by wiring that passes under the heater 310 and which is not visible in FIG. 6.)

The heater 310 comprises a heating element formed from a sintered metal fiber material and is generally in the form of a sheet or porous, conducting material (such as steel). However, it will be appreciated that other porous conducting materials may be used. The overall resistance of the heating element in the example of FIG. 6 is around 1 ohm. However, it will be appreciated that other resistances may be selected, for example having regard to the available battery voltage and the desired temperature/power dissipation characteristics of the heating element. In this regard, the relevant characteristics may be selected in accordance with the desired aerosol (vapor) generation properties for the device depending on the source liquid of interest.

The main portion of the heating element is generally rectangular with a length (i.e. in a direction running between the connector 31B and the contact 632A) of around 20 mm and a width of around 8 mm. The thickness of the sheet comprising the heating element in this example is around 0.15 mm.

As can be seen in FIG. 6, the generally-rectangular main portion of the heating element has slots 311 extending inwardly from each of the longer sides. These slots 311 engage pegs 312 provided by vaporizer housing component 627B, thereby helping to maintain the position of the heating element in relation to the housing components 627A, 627B.

The slots 311 extend inwardly by around 4.8 mm and have a width of around 0.6 mm. The slots 311 extending inwardly are separated from one another by around 5.4 mm on each side of the heating element, with the slots extending inwardly from the opposing sides being offset from one another by around half this spacing. A consequence of this arrangement of slots is that current flow along the heating element is in effect forced to follow a meandering path, which results in a concentration of current and electrical power around the ends of the slots. The different current/power densities at different locations on the heating element mean there are areas of relatively high current density that become hotter than areas of relatively low current density. This in effect provides the heating element with a range of different temperatures and temperature gradients, which can be desirable in the context of aerosol provision systems. This is because different components of a source liquid may aerosolize/vaporize at different temperatures, and so providing a heating element with a range of temperatures can help simultaneously aerosolize a range of different components in the source liquid.

The heater 310 shown in FIG. 6, having a substantially planar shape which is elongated in one direction, is well-suited to act as an antenna. In conjunction with the metal housing 202 of the control unit 20, the heater 310 forms an approximate dipole configuration, which has a physical size of the same order of magnitude as the wavelength of Bluetooth® Low Energy communications—i.e. a size of several centimeters (allowing for both the heater 310 and the metal housing 202) against a wavelength of around 12 cm.

Although FIG. 6 illustrates one shape and configuration of the heater 310 (heating element), the skilled person will be aware of various other possibilities. For example, the heater 310 may be provided as a coil or some other configuration of resistive wire. Another possibility is that the heater 310 is configured as a pipe containing liquid to be vaporized (such as some form of tobacco product). In this case, the pipe may be used primarily to transport heat from a place of generation (e.g. by a coil or other heating element) to the liquid to be vaporized. In such a case, the pipe still acts as a heater in respect of the liquid to be heated. Such configurations can again optionally be used as an antenna to support wireless configurations.

As was noted previously herein, a suitable e-cigarette 10 can communicate with a mobile communication device 400, for example by paring the devices using the Bluetooth® low energy protocol.

Consequently, it is possible to provide additional functionality to the e-cigarette 10 and/or to a system comprising the e-cigarette 10 and the smartphone 400, by providing suitable software instructions (for example in the form of an app) to run on the smartphone 400.

Figure 7:
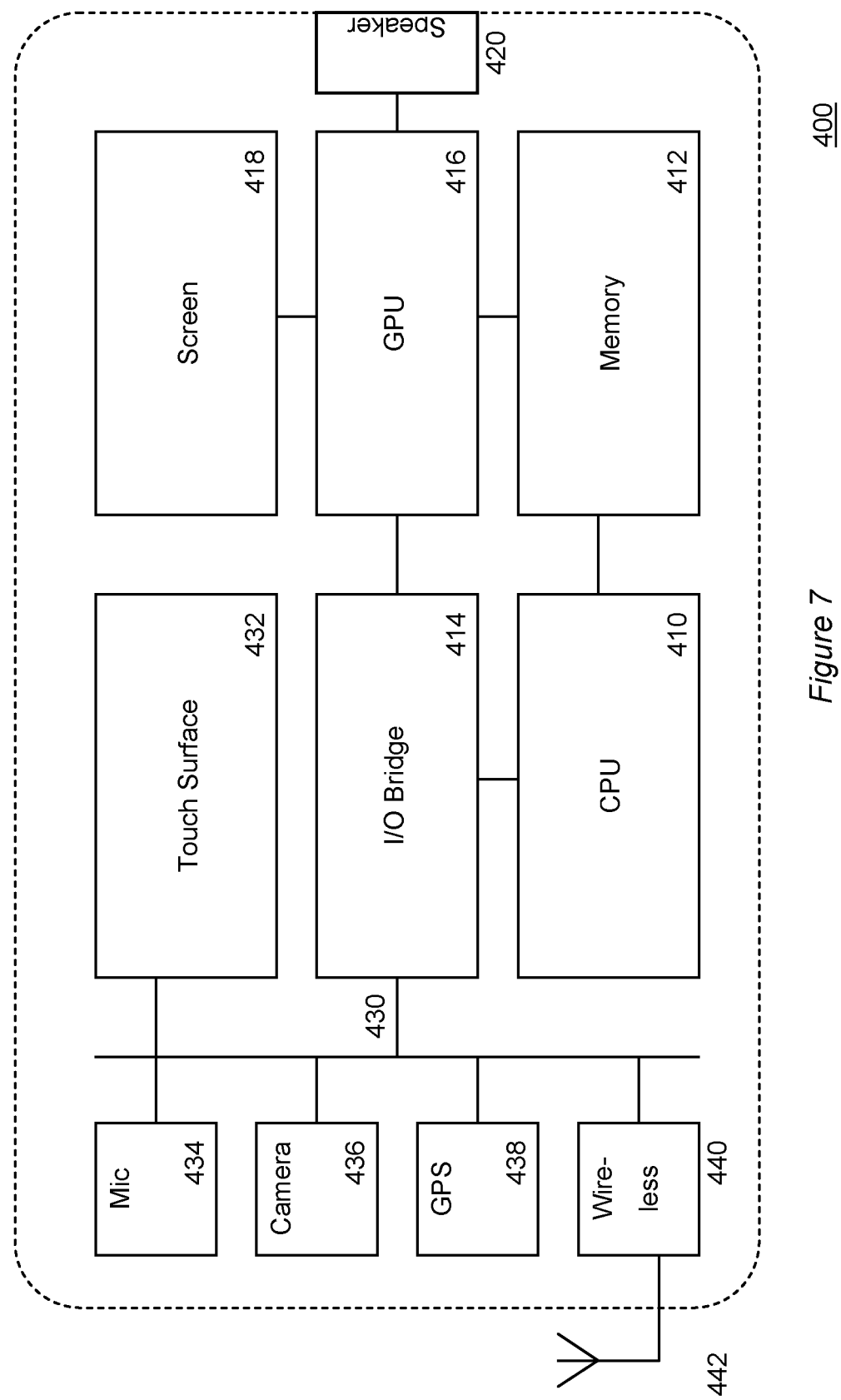
FIG. 7 is a schematic diagram of a mobile communication device in accordance with some embodiments of the disclosure.

Turning now to FIG. 7, a typical smartphone 400 comprises a central processing unit (CPU) (410). The CPU 410 may communicate with components of the smartphone 400 either through direct connections or via an I/O bridge 414 and/or a bus 430 as applicable.

In the example shown in FIG. 7, the CPU 410 communicates directly with a memory 412, which may comprise a persistent memory such as for example Flash® memory for storing an operating system and applications (apps), and volatile memory such as RAM for holding data currently in use by the CPU 410. Typically persistent and volatile memories are formed by physically distinct units (not shown). In addition, the memory 412 may separately comprise plug-in memory such as a microSD card, and also subscriber information data on a subscriber information module (SIM) (not shown).

The smartphone 400 may also comprise a graphics processing unit (GPU) 416. The GPU 416 may communicate directly with the CPU 410 or via the I/O bridge, or may be part of the CPU 410. The GPU 416 may share RAM with the CPU 410 or may have its own dedicated RAM (not shown) and is connected to the display 418 of the smartphone 400. The display is typically a liquid crystal (LCD) or organic light-emitting diode (OLED) display, but may be any suitable display technology, such as e-ink. Optionally the GPU 416 may also be used to drive one or more loudspeakers 420 of the smartphone 400.

Alternatively, the speaker 420 may be connected to the CPU 410 via the I/O bridge 414 and the bus 430. Other components of the smartphone 400 may be similarly connected via the bus 430, including a touch surface 432 such as a capacitive touch surface overlaid on the screen for the purposes of providing a touch input to the device, a microphone 434 for receiving speech from the user, one or more cameras 436 for capturing images, a global positioning system (GPS) unit 438 for obtaining an estimate of a geographical position of the smartphone 400, and wireless communication means 440.

The wireless communication means 440 may in turn comprise several separate wireless communication systems adhering to different standards and/or protocols, such as Bluetooth® (standard or low-energy variants), near field communication and Wi-Fi® as described previously, and also phone based communication such as 2G, 3G and/or 4G.

The systems are typically powered by a battery (not shown) that may be chargeable via a power input (not shown) that in turn may be part of a data link such as USB (not shown).

It will be appreciated that different smartphones may include different features (for example a compass or a buzzer) and may omit some of those listed above (for example a touch surface).

Thus more generally, in an embodiment of the present disclosure a suitable remote device such as smartphone 400 will comprise a CPU 410 and a memory 412 for storing and running an app, and wireless communication means operable to instigate and maintain wireless communication with the e-cigarette 10. It will be appreciated however that the remote device may be any device that has these capabilities, such as a tablet, laptop, smart TV or the like.

Figure 8:
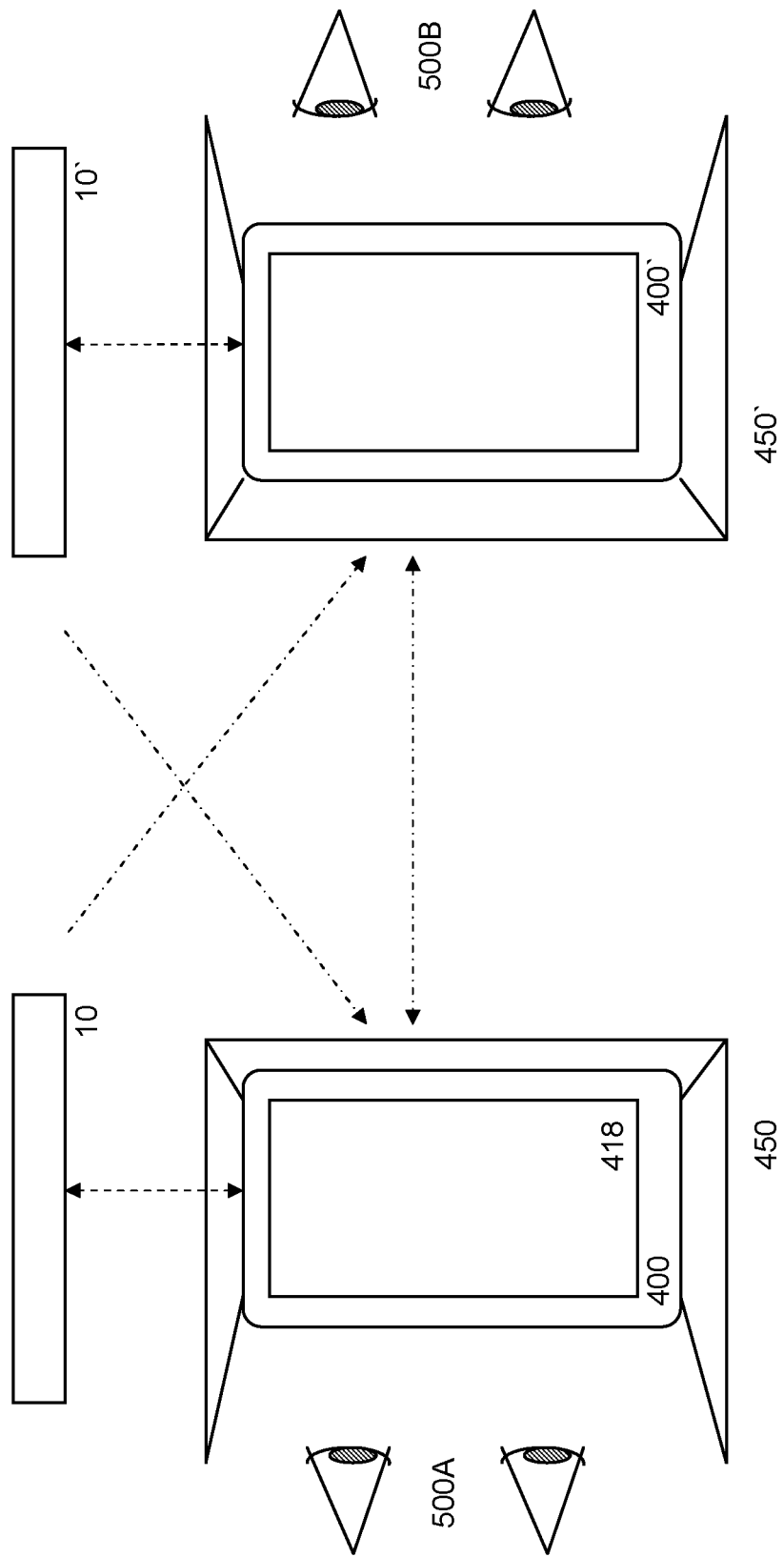
FIG. 8 is a schematic diagram of a visualization system in accordance with some embodiments of the disclosure.

Referring to FIG. 8, one example of additional functionality that may be provided by a combination of the e-cigarette 10 and a remote device such as the mobile communication device 400 is a method of visualization between the e-cigarette 10 and the mobile communication device 400 of a user 500A.

In this case, the mobile communication device 400 may operate as a virtual reality device, for example by being held within a head-mounted unit 450, in a predetermined position in relation to the eyes of the user and/or any intervening optics used to enable the user to focus on the display of the mobile communication device 400 at this proximity (not shown).

The mobile communication device 400 may similarly operate as an augmented reality device, either by supplying a view of the real world from a rear-mounted camera to its display within the above head-mounted unit, or by being arranged in an adapted head mounted unit with suitable optics (such as a semi-transparent mirror) to enable simultaneous view of the real world and its display.

It will be appreciated that the mobile communication device 400 is only an example of a remote device operating as a virtual reality device or augmented reality device capable of receiving data from the e-cigarette 10 and providing some form of associated visualization. In practice, any virtual reality device or augmented reality device with this capability may be suitable (for example a virtual reality device such as the Oculus Rift® or Samsung Gear VR® devices, or an augmented reality device such as the Google Glass® or Microsoft Hololens® devices), and hence more generally such a device may be referred to as a "visualization device."

In an embodiment of the present disclosure, the e-cigarette 10 and the visualization device (400, 450) operate as a system for producing a virtual reality vapor for the e-cigarette 10 that is substantially synchronized with the real vapor exhaled by the user. The virtual reality vapor may be of particular use where exhalation of e-cigarette vapor does not result in a visible "cloud," or where a user wishes to vape whilst using the visualization device (400, 450) for other purposes. Conversely, the virtual reality vapor may counterintuitively be useful in augmenting a physically visible cloud of vapor, for example color coding it according to temperature or a liquid flavor, or adding graphical effects. There is also scope for social and novel virtual interactions.

It will be appreciated that a virtual reality vapor is a computer graphic intended to correspond in some manner to an exhaled vapor cloud. The same virtual reality vapor may be used in a virtual reality display (where the real world is not visible, and typically a virtual world is displayed) and also may be used superposed over a view of the real world in an augmented reality display. Hence a virtual reality vapor may be equally used for virtual and augmented reality applications.

As noted above, the e-cigarette 10 is able to communicate with the visualization device (400, 450), for example via Bluetooth®. When the user operates the e-cigarette 10, for example by inhaling, then the e-cigarette 10 informs the visualization device (400, 450) that inhalation has occurred. This may occur at the start of inhalation or, for example at the end of the inhalation to indicate that inhalation is complete, and may optionally include additional data such as an indication of the size of inhalation; for example the duration of the inhalation and/or the average or integrated airflow during the inhalation may be taken to indicate the size of inhalation. For button-activated devices, notification that inhalation has occurred may happen when the button is activated, and/or notification that inhalation has occurred and is complete may happen when the button is deactivated (i.e. no longer pressed), as these are proxy indicators that inhalation of vapor from the e-cigarette has started or stopped.

The visualization device (400, 450) (which itself may be in communication with a separate computing system, not shown, to provide graphics, processing or other computing services) then displays a virtual vapor cloud that is substantially synchronized with the real-time exhalation of the user.

The real-time exhalation of the user may be detected by suitable sensors on either the e-cigarette 10 or the visualization device (400, 450). Example sensors include one or more touch sensors on a mouthpiece of the e-cigarette 10, to detect loss of contact with the user's mouth as a preparatory act to exhalation. Similarly, an accelerometer in the e-cigarette 10 may be used to detect a motion of the e-cigarette 10 characteristic of it being removed from the user's mouth.

Meanwhile, the visualization device (400, 450) may comprise a microphone and access to processing means operable to detect the sound of exhalation. Similarly, the visualization device (400, 450) may comprise a camera and access to processing means operable to detect the removal of the e-cigarette 10 from the user's mouth, and/or the start of a visible plume of vapor being emitted from the user's mouth or nose. Other detection mechanisms may be envisaged that may operate separately or in combination with any of those described herein, including a heat detector to detect vapor exhaled by the user (optionally at a temperature above normal breath temperature) or similarly a humidity detector to detect vapor exhaled by the user (optionally at a local humidity above normal breath humidity); the normal values here may be assumed or calibrated to the user.

In any event, upon detecting the beginning of exhalation, the visualization device (400, 450) can then provide a visualization of a virtual plume of vapor, as described later herein. Optionally, the size and/or velocity (or some other feature, such as color) of the virtual reality vapor may be a function of the size of the original inhalation.

However, the above approach has some problems.

Not all users remove an e-cigarette 10 to exhale, making touch- or motion-based detection unreliable. Meanwhile, video-based detection of motion or vapor is computationally costly, reducing battery life for a portable device such as a mobile communication device acting as a visualization device. Meanwhile analysis of a microphone signal is prone to false positives that sound like exhalation, such as wind noise, or the sound of voices (in particular fricatives or "ess" sounds). It would be disconcerting and undesirable for a user to be unexpectedly presented with virtual plumes of vapor that are not clearly related to the user's own exhalation.

However, contrary to these detection problems, one predictable outcome of how a user interacts with their e-cigarette 10 is that once they have inhaled on the e-cigarette 10, they must eventually exhale. Moreover, in normal use this exhalation will occur within a predictable time frame.

Hence, in an embodiment of the present disclosure, to a first approximation a typical or average delay between inhalation and exhalation of a user can be assumed, so that a timing of the user's exhalation can be estimated without any external detection of the exhalation using sensors such as those described above.

To a second approximation, the typical delay between inhalation and exhalation can be estimated as a function of one or more biometric factors such as the height, weight, age and/or gender of the user, which may be provided during a registration phase of using the visualization device, or be otherwise available (for example via an account used with one or more apps relating to the e-cigarette).

To a third approximation, the typical delay between inhalation and exhalation can be estimated as a function of the size of inhalation, indicated as described previously, optionally in conjunction with one or more of the height, weight, age and/or gender of the user, obtained as described above.

To a fourth approximation, the typical delay between inhalation and exhalation can be measured for the particular user, for example by initially using reliable but computationally costly methods such as video analysis (or any of the sensor methods described previously herein if the user is made aware of the method employed, for example via an on-screen message) during a calibration period. This measure may be refined further to be modeled as a function of inhalation size. After the calibration period, the sensor method is no longer needed.

Notably, with the user's co-operation, such a calibration period does not need to rely on complex sensors, or sensors provided only for a calibration purpose. For example, the user could be asked to press an existing button on the e-cigarette or the visualization device as they exhale, or if there are touch or motion sensors, to reliably remove the e-cigarette 10 from their mouth during the calibration phase. Only timing measurements for those occasions when the user remembers to do so would be used, for example based on a time-out threshold. Optionally, statistical outliers (or example more than 1 standard deviation from a mean delay for a particular measure) may be discarded.

In addition, any of the above approximations may be provided separately for different (e-)liquids, as vapors from different liquids may be held in the lungs for different periods of time. These may be separately measured, or different liquids may have an associated multiplier provided or estimated by calibration to increase or decrease an established set of delay(s). Similarly, separate approximations may be provided for different strength/vapor provision level settings, or may be included as part of a delay model in a similar manner to the size of inhalation.

The visualization device may thus hold default look-up tables of one or more inhalation-exhalation delay times, optionally for one or more sizes of inhalation, and/or optionally for one or more liquids, optionally modifiable to the individual user by a calibration process.

The visualization device may then use the appropriate delay after receiving notice from the e-cigarette 10 that inhalation has been completed (optionally with an indication of the inhalation size) to estimate when to display the virtual reality vapor to the user.

In this way, the system is able to display a virtual reality vapor responsive to timing made with respect to inhalation on the e-cigarette 10 by the user.

Advantageously, the above embodiment can therefore enable a virtual or augmented reality experience for any user having an e-cigarette 10 with basic inhalation-notification means (e.g. via Bluetooth®) and a visualization device, only requiring suitable software for the visualization device to operate in the desired manner. In this case there is no need to physically adapt the e-cigarette 10 (e.g. to add an accelerometer) or the visualization device (e.g. to add a camera capable of viewing the e-cigarette 10 when the visualization device is being worn).

However, given such a reasonably accurate model of the user's inhalation/exhalation patterns, it is also possible to refine the above embodiment to make use of any suitable sensors that are available on the e-cigarette and/or visualization device.

In particular, given a reasonably accurate estimation of the time when exhalation will begin, based on one of the first to fourth approximations described above, a detection window centered on this time may be used, during which one or more sensors are monitored to detect exactly when (to the degree of accuracy possible by a respective sensor) exhalation starts. This may improve the perceived accuracy of synchronization of the real and virtual exhalations.

Hence for example, video detection may be used during a short window centered on the estimated time; the computational load of the video processing is therefore limited to the windowed period, providing a good trade-off between accuracy and computational load/battery life.

Alternatively or in addition, microphone detection may be used during a short window (potentially of different duration to that used for video detection) centered on the estimated time; the chances of a false-positive detection of an exhalation noise is therefore limited to the windowed period (during which an exhalation is extremely likely in any case), again providing a good trade-off between accuracy and unexpected displays of virtual vapor.

The "short" window may be an absolute period, such as a period in the range 0.05-2.0 seconds, or it may be a proportion of the estimated delay, such as a period in the range +/−1-30% of the delay or one standard deviation from a mean value for the delay.

Instead of being centered, the window may be asymmetrically positioned with respect to the expected time of exhalation; if the exhalation starts before the window begins, the sensor(s) should immediately detect it when the window begins. By contrast if the exhalation starts after the window ends, then there is no scope for detection. Hence biasing the window to detect late exhalations may improve overall detection rates.

Alternatively or in addition, the visualization system may display the virtual reality vapor at the end of the detection window whether or not exhalation was detected, on the basis that exhalation must occur and, based on the estimated time for exhalation, it is overdue by the end of the window period.

It will be appreciated that use of the sensors to detect the timing of exhalations in this way can also allow for ongoing refinement of estimated delay times in a manner similar to the above described calibration stage, during ongoing use.

Whether based solely on estimated timing, or based on detection during a detection window bounding the estimated timing, the visualization device may then display a virtual reality vapor.

It will be appreciated that the virtual reality vapor may be a computer graphic designed to look like real vapor, but is not limited to this. For example the vapor may change color randomly or in response to data such as inhalation size, or it may resemble flames or sparks, or may relate to the particular liquid being used; for example showing a flurry of petals or mint leaves. Indeed any graphical image(s) may be used in this manner, such as a corporate logo, design or trademark, selected photos of the user (for example on their phone's gallery), virtual stickers or trophies collected for meeting some activity criterion, musical notations (optionally driven by music playing on the visualization device), etc. Equally, a single graphic may be scaled, rotated, moved and/or have its transparency increased so as to appear to diffuse away from a point of origin.

Hence it will be appreciated that the term "virtual reality vapor" is not limited to graphics that appear to be vapors, and may be more generally thought of as a dispersion of one or more graphical objects (vapor primitives or other graphical objects) into a virtual space from an origin position typically corresponding with the user's mouth.

The above embodiments relate to a user's own virtual or augmented experience of a virtual reality vapor, but embodiments of the disclosure need not be limited to this.

Referring again to FIG. 8, notification that a first user 500A has inhaled on an e-cigarette 10 may be transmitted to the visualization device of the first user 500A and/or the visualization device of a second user 500B, and potentially vice-versa. Hence for example first e-cigarette 10 may communicate with first visualization device (400, 450), but may also communicate with second visualization device (400', 450'), either by also being paired with this second device, or by using an unpaired broadcast protocol such as Bluetooth® Broadcast.

In this case, both visualization devices (400, 450, 400', 450') may then independently estimate the exhalation time of the first user to general virtual reality vapors to display to their respective users.

However, it will be appreciated that the second visualization device (400', 450') is less likely to produce an accurate timing for such an exhalation, either because it does not have a calibrated model of the first user's inhalation-exhalation patterns (or similarly a set of their biometric factors), or because it is less able to make use of sensors during a detection period, for example being too far from the first user to reliably detect the sound of exhalation.

Hence alternatively or in addition, the first visualization device (400, 450) may transmit an exhalation timing signal to the second visualization device (400', 450'). The exhalation timing signal may be the estimate of when exhalation will occur that (which the first visualization device 400, 450 will use to drive its virtual graphics), or it may be an indicator that exhalation has been detected, depending on how the first visualization device 400, 450 is currently operating.

In this way, a second user, who may or may not themselves use an e-cigarette 10, may optionally see a virtual vapor substantially synchronized with the exhalation of a first user. Notably the first user themselves may or may not be using a visualization device at the time, although synchronization is likely to be more accurate if they are, as explained above.

Hence more generally, a given user of a virtual or augmented reality head mounted display in accordance with an embodiment of the present disclosure may see a virtual vapor substantially synchronized with the exhalation of one or more users of e-cigarettes in the vicinity.

The positioning of virtual vapor at another user's location is potentially more complex than generating virtual vapor for the user themselves; for the user's own exhalations, the source of the vapor is in a fixed position in relation the their eyes (i.e. just below). Meanwhile, a second user's mouth may be in an arbitrary position relative to the first user. However, the second user is using another visualization device, it may transmit position or motion data that enables localization of the device, or it may provide markings or lights that enable visual tracking of the visualization device. This would enable an estimation of the position of the second user's face. Similarly, the position of a light on the end of an e-cigarette may be tracked to estimate the position of the second user's mouth. To assist tracking, a visualization device may communicate with the e-cigarette to change a property of the light (e.g. color or blinking pattern) to disambiguate the e-cigarette from other lights visible in the environment.

It will be appreciated that a visualization device can simultaneously be a first visualization device and a second visualization device, in the sense of transmitting data relating to the vaping of their own user and also receiving data relating to the vaping of one or more other users, for the purposes of displaying virtual reality vapor for more than one user.

Figure 9:
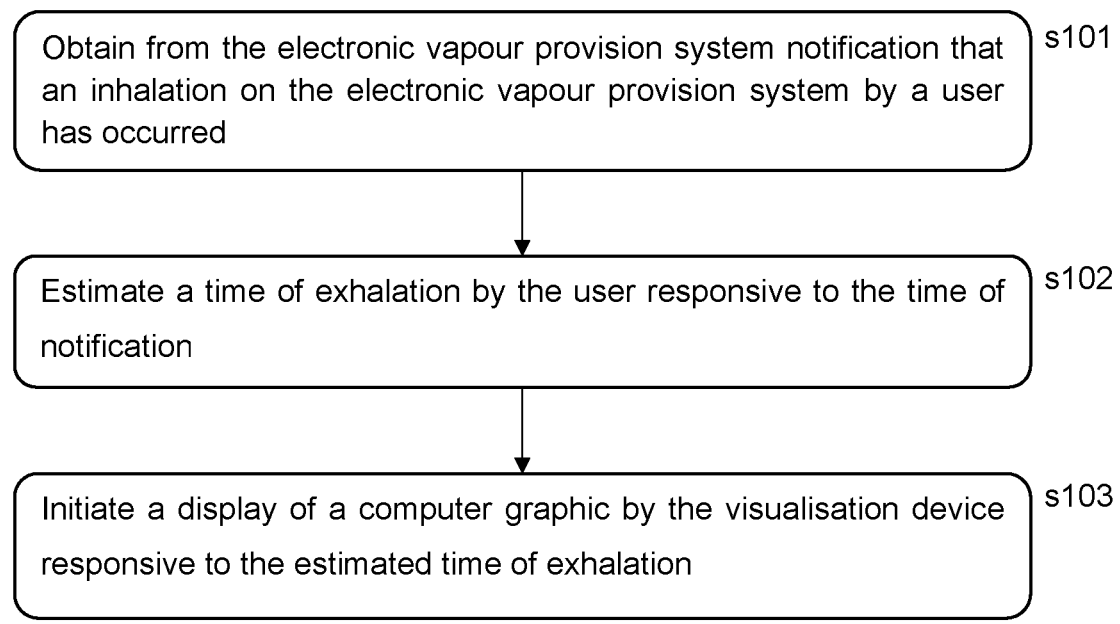
FIG. 9 is a flow diagram of a method of visualization between an electronic vapor provision system and a mobile communication device of a first user in accordance with some embodiments of the disclosure.

Referring now to FIG. 9, in a summary embodiment of the present disclosure, a method of visualization between an electronic vapor provision system (10) and a visualization device (400, 450), comprises:

At s101, obtaining from the electronic vapor provision system notification that an inhalation on the electronic vapor provision system by a user has occurred. As explained previously herein, for example a signal may be sent using Bluetooth® between an e-cigarette and a smartphone acting as a VR or AR display.

At s102, estimating a time of exhalation by the user responsive to the time of notification. As explained previously herein, for example the estimate may be to one of several levels of approximation, and/or may be responsive to direct detection within a detection window; and At s103, initiating a display of a computer graphic by the visualization device responsive to the estimated time of exhalation. As explained previously herein, the computer graphic may show the dispersion of one or more arbitrary graphic elements within a virtual space.

It will be apparent to a person skilled in the art that variations in the above method corresponding to operation of the various embodiments of the apparatus as described and claimed herein are considered within the scope of the present disclosure, including but not limited to:

- estimating a time of exhalation comprising adding a delay to the time of notification, the delay being a predetermined average delay between inhalation and exhalation;
- estimating a time of exhalation comprising adding a delay to the time of notification, the delay being estimated as a function of one or more biometric factors of the user;
- estimating a time of exhalation comprising adding a delay to the time of notification, the delay being based upon delay calibration data obtained during a calibration phase;
- the delay being estimated as a function of inhalation size;
- the delay being estimated as a function of vapor provision level;
- the delay being estimated responsive to a type of liquid being vaporized;
- setting a detection period responsive to the estimated time of exhalation, and estimating a time of exhalation by the user by detecting an exhalation of the user within the detection period;
- in this case, detecting may comprise one or more of:
  i. detecting loss of contact of the electronic vapor provision system with the user's mouth;
  ii. detecting a characteristic motion of the electronic vapor provision system;
  iii. detecting a sound indicative of exhalation; and
  iv. detecting a visual indication of exhalation;
- notification that inhalation on an electronic vapor provision system of a first user has occurred is obtained by a visualization device of a second user; and
- a visualization device of a first user transmits an exhalation timing signal to a visualization device of a second user.

It will be appreciated that alternatively or in addition, the direct exhalation of the vapor by the user may be detected using a the techniques described herein without relying on a notification of inhalation from the electronic vapor provision system or estimating the time of exhalation by the user.

Accordingly, a method of visualization between an electronic vapor provision system and a visualization device may comprise the steps of detecting an exhalation of vapor by a user, and initiating a display of a computer graphic by the visualization device responsive to the detected exhalation.

It will be appreciated that the any of the methods described herein may be carried out on conventional hardware suitably adapted as applicable by software instruction or by the inclusion or substitution of dedicated hardware.

Thus the required adaptation to existing parts of a conventional equivalent device may be implemented in the form of a computer program product comprising processor implementable instructions stored on a tangible non-transitory machine-readable medium such as a floppy disk, optical disk, hard disk, PROM, RAM, flash memory or any combination of these or other storage media, or realized in hardware as an ASIC (application specific integrated circuit) or an FPGA (field programmable gate array) or other configurable circuit suitable to use in adapting the conventional equivalent device. Separately, such a computer program may be transmitted via data signals on a network such as an Ethernet, a wireless network, the Internet, or any combination of these of other networks.

Hence for example electronic vapor provision system as described herein may comprise an inhalation detection means adapted to detect when inhalation is complete, and a wireless transmission means, wherein the electronic vapor provision system is adapted (for example by suitable software instruction) to transmit a notification that an inhalation on the electronic vapor provision system by a user has occurred when the inhalation is complete.

Similarly a visualization device as described herein may comprise wireless reception means adapted (for example by suitable software instruction) to receive from an electronic vapor provision system notification that an inhalation on the electronic vapor provision system by a user has occurred, time estimation processing means adapted (for example by suitable software instruction) to estimate a time of exhalation by the user responsive to the time of notification, and display means adapted (for example by suitable software instruction) to display of a computer graphic responsive to the estimated time of exhalation, initiating a display of a computer graphic by the visualization device responsive to the estimated time of exhalation.

The electronic vapor provision system and the visualization device together may thus form a visualization system.

Again it will be appreciated that alternatively or in addition, the direct exhalation of the vapor by the user may be detected using a the techniques described herein without relying on a notification of inhalation from the electronic vapor provision system or estimating the time of exhalation by the user. Accordingly, a visualization device may comprise an exhalation detection means adapted to detect exhalation of vapor by a user, and display means adapted to display a computer graphic responsive to the detected exhalation.

In order to address various issues and advance the art, this disclosure shows by way of illustration various embodiments in which the claimed invention(s) may be practiced. The advantages and features of the disclosure are of a representative sample of embodiments only, and are not exhaustive and/or exclusive.

For example, for convenience the present application mainly refers to the liquid variety of electronic vapor provision system, but the invention clearly also applies to tobacco heating products and the like.

The embodiments are presented only to assist in understanding and to teach the claimed invention(s). It is to be understood that advantages, embodiments, examples, functions, features, structures, and/or other aspects of the disclosure are not to be considered limitations on the disclosure as defined by the claims or limitations on equivalents to the claims, and that other embodiments may be utilized and modifications may be made without departing from the scope of the claims. Various embodiments may suitably comprise, consist of, or consist essentially of, various combinations of the disclosed elements, components, features, parts, steps, means, etc other than those specifically described herein. The disclosure may include other inventions not presently claimed, but which may be claimed in future.

The invention claimed is:

1. A method of visualization between an electronic vapor provision system and a visualization device, comprising:
   obtaining from the electronic vapor provision system notification that an inhalation on the electronic vapor provision system by a user has occurred;
   estimating a time of exhalation by the user responsive to a time of the notification; and
   initiating a display of a computer graphic by the visualization device responsive to the estimated time of exhalation.

2. A method according to claim 1, wherein the estimating a time of exhalation comprises adding a delay to the time of the notification, the delay being a predetermined average delay between inhalation and exhalation.

3. A method according to claim 1, wherein the estimating a time of exhalation comprises adding a delay to the time of the notification, the delay being estimated as a function of one or more biometric factors of the user.

4. A method according to claim 1, wherein the estimating a time of exhalation comprises adding a delay to the time of the notification, the delay being based upon delay calibration data obtained during a calibration phase.

5. A method according to claim 2, in which the delay is estimated as a function of inhalation size.

6. A method according to claim 2, in which the delay is estimated as a function of vapor provision level.

7. A method according to claim 2, in which the delay is estimated responsive to a type of liquid being vaporized.

8. A method according to claim 1, further comprising:
   setting a detection period responsive to the estimated time of exhalation; and
   estimating the time of exhalation by the user by detecting an exhalation of the user within the detection period.

9. A method according to claim 8, wherein the detecting comprises one or more selected from the group consisting of:
   detecting loss of contact of the electronic vapor provision system with a mouth of the user;
   detecting a characteristic motion of the electronic vapor provision system;
   detecting a sound indicative of exhalation; and
   detecting a visual indication of exhalation.

10. A method according to claim 1, wherein:
    notification that inhalation on an electronic vapor provision system of a first user has occurred is obtained by a visualization device of a second user.

11. A method according to claim 1, wherein: .
    a visualization device of a first user transmits an exhalation timing signal to a visualization device of a second user.

12. A method of visualization between an electronic vapor provision system and a visualization device, comprising:
    detecting an exhalation of vapor by a user; and
    initiating a display of a computer graphic by the visualization device responsive to the detected exhalation.

13. A non-transitory computer-readable storage medium storing a computer program for implementing the method of claim 1.

14. An electronic vapor provision system, comprising:
    an inhalation detection means adapted to detect when inhalation has occurred; and
    a wireless transmission means,
    wherein the electronic vapor provision system is adapted to transmit a notification that an inhalation on the electronic vapor provision system by a user has occurred.

15. A visualization device, comprising:
    wireless reception means adapted to receive from an electronic vapor provision system notification that an inhalation on the electronic vapor provision system by a user has occurred;
    time estimation processing means adapted to estimate a time of exhalation by the user responsive to a time of the notification; and
    display means adapted to display a computer graphic responsive to the estimated time of exhalation.

16. A visualization device, comprising
    an exhalation detection means adapted to detect exhalation of vapor by a user; and
    display means adapted to display a computer graphic responsive to the detected exhalation.

17. A visualization visualisation system, comprising:
    an electronic vapor provision system comprising:
        an inhalation detection means adapted to detect when inhalation has occurred, and
        a wireless transmission means,
        wherein the electronic vapor provision system is adapted to transmit a notification that an inhalation on the electronic vapor provision system by a user has occurred; and
    a visualization device comprising:
        wireless reception means adapted to receive from the electronic vapor provision system the notification that an inhalation on the electronic vapor provision system by a user has occurred;
        time estimation processing means adapted to estimate a time of exhalation by the user responsive to a time of the notification; and
        display means adapted to display a computer graphic responsive to the estimated time of exhalation.

* * * * *